United States Patent [19]

Kirmann

[11] Patent Number: Plant 6,019

[45] Date of Patent: Sep. 22, 1987

[54] GERANIUM PLANT NAMED JOSY

[75] Inventor: Wolfgang Kirmann, Langenzersdorf, Austria

[73] Assignee: Mirko Vavra, Bisamberg, Austria

[21] Appl. No.: 811,116

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Josy having rose-pink flower color, with very dark red variegation on the upper petals; dark green foliage; very early flowering; good bud production at night temperatures up to 16° C., thus providing a long and continuous flowering period; compact, self-branching growth habit; and ease of propagation and good rooting habit.

3 Drawing Figures

The present invention comprises a new and distinct cultivar of geranium, botanically known as *Pelargonium domesticum,* and hereinafter referred to by the cultivar name Josy.

Josy is a product of a planned breeding program which had the objective of creating new geranium cultivars having a compact growth habit, early flowering and long flowering period, good flower production, relatively small foliage and pale rose-pink flower color.

Josy was originated from a hybridization made by applicant in a controlled breeding program in Bisamberg, Austria in 1977. The female parent was Morgengruss, a cultivar characterized by its compact, broad growth habit, light pink flower color with red eyes, and medium early flowering. The male parent of Josy was a cultivar designated as seedling 2/76 having a very vigorous growth habit, good flower production and rose-pink flower color.

Josy was discovered and selected as one flowering plant within the progeny of the stated cross by applicant on Feb. 25, 1978 in a controlled environment in Bisamberg, Austria.

The first act of asexual reproduction of Josy was accomplished when vegetative cuttings were taken from the initial selection on Aug. 27, 1978 in a controlled environment in Bisamberg, Austria by a technician working under formulations established and supervised by Wolfgang Kirmann. Horticultural examination of selected units initiated in the spring of 1979 has demonstrated that the combination of characteristics as herein disclosed for Josy are firmly fixed and are retained through successive generations of asexual reproduction.

Josy has not been observed under all possible environmental conditions. The phenotype may vary significantly with variations in environment such as temperature, light intensity, and day length. The following observations, measurements and comparisons describe plants grown in Bisamburg, Austria under conditions which approximate those generally used in commercial practice.

The following traits have been repeatedly observed and are determined to be basic characteristics of Josy, which in combination distinguish this geranium as a new and distinct cultivar.

1. Pale rose-pink flower color, variegated with very dark red on upper petals.

2. Propagates well, with very good rooting habit.
3. Strong, dark green foliage.
4. Compact, self-branching growth habit resulting in the setting of many buds.
5. Very early flowering and long flowering period.
6. Buds are produced under normal greenhouse conditions (5000 Lux for 16 hours per day) at 14°–16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.
7. Josy is unique with regard to the combined features of compactness, continuous flowering, floriferous habit, and pale rose-pink flower color.

Of the many commercial cultivars known to the present inventor, the most similar in comparison to Josy is Quichita, an unpatented but commercial cultivar. In comparison to Quichita, Josy has a more compact growth habit, flowers earlier and has better flower production, and has a more brilliant color.

The accompanying photographic drawings show typical flower and foliage characteristics of Josy, with colors being as true as possible with illustrations of this type.

Sheet 1 is a perspective view of a potted plant of Josy.

Sheet 2 is a black and white print showing the top surface of immature and mature plants of Josy.

Sheet 3 is a black and white print showing the under surface of immature and mature plants of Josy.

In the following description color references are made to The Royal Horticultural Society Colour Chart (RHS). The color values were determined at 9:00 a.m. on May 23, 1985 under 35,000 Lux light intensity in a greenhouse at Hillscheid, Federal Republic of Germany.

Classification:

*Botanical.*—*Pelargonium domesticum.*

*Commercial.*—Commonly referred to as a "Martha Washington" geranium, and having the cultivar name Josy.

INFLORESCENCE

A. Umbel:

*Average diameter.*—Relatively large, 95–120 mm.

*Peduncle length.*—Short.

*Pedicel length.*—Normal.

B. Corolla:

*Average diameter.*—65–80 mm; total inflorescence diameter is within the foliage.

*Form.*—Five-six petals; symmetric.

*Color (general tonality from a distance of three meters).*—Rose-pink with deep red variegation on the upper petals.

*Color (upper surface).*—62C-D, variegated with 53A-B on upper petals and 53B at approximate center of lower petals.

C. Bud:

*Shape.*—Stocky, oval.

*Color.*—White with pink.

D. Reproductive organs:

*Androecium.*—Red-yellow.

*Gynoecium.*—Five to seven part.

E. Spring flowering response period: Very early.

F. Durability: Very good.

PLANT

A. Foliage:

*Form.*—Zygomorphic with a nectar spur.

*Margin.*—Sharply crenate, with indentation.

*Color (upper surface).*—Dark green.

*Tolerance of Botrytis and soil fungi.*—Very good.

B. General appearance and form:

*Internode length.*—Short.

*Branching pattern.*—Good.

*Height.*—Compact.

I claim:

1. A new and distinct cultivar of geranium named Josy, as described and illustrated, and particularly characterized by its rose-pink flower color with very dark red variegation on upper petals; dark green foliage; very early flowering; good bud production at night temperatures up to 16° C., thus providing a long and continuous flowering period; compact, self-branching growth habit; and by its ease of propagation and good rooting habit.

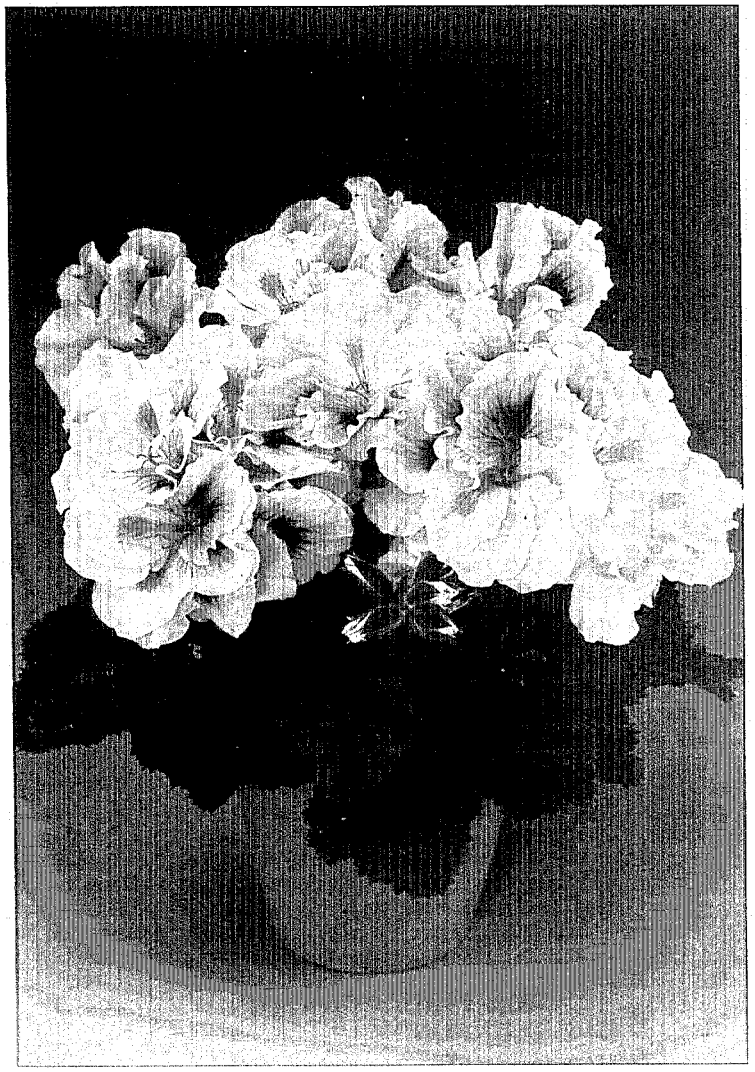

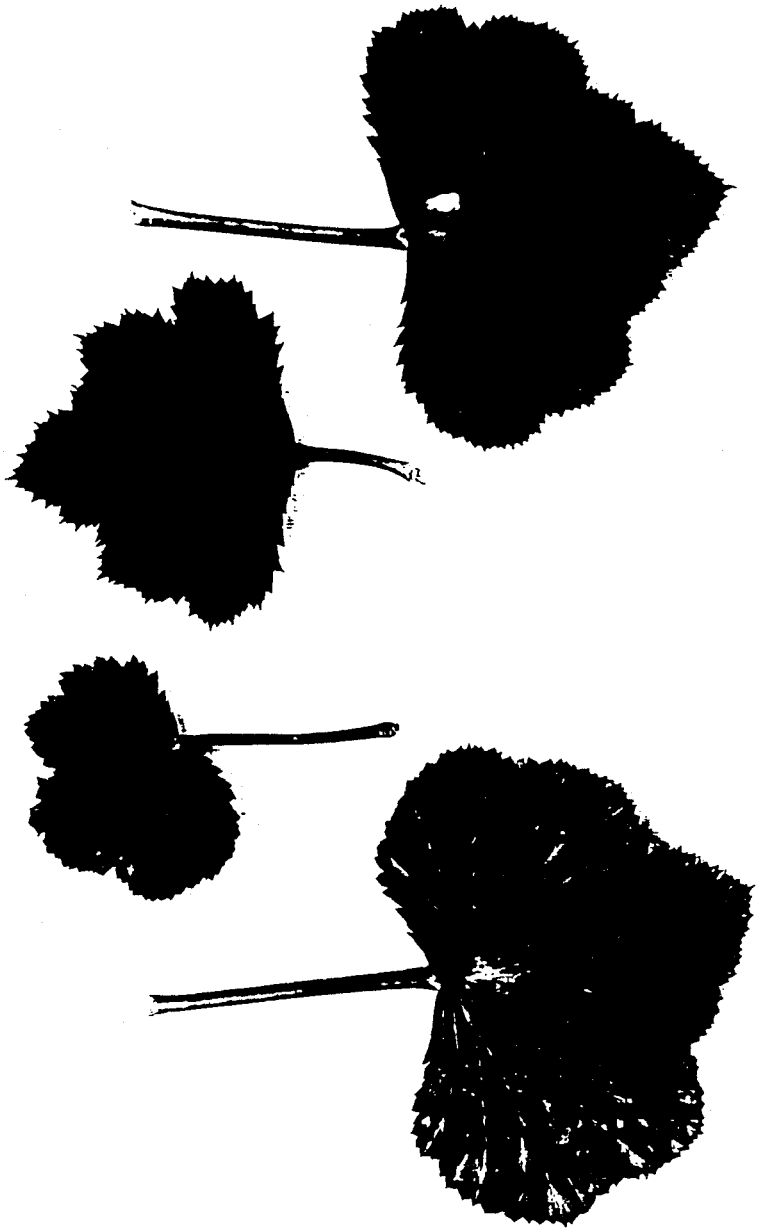

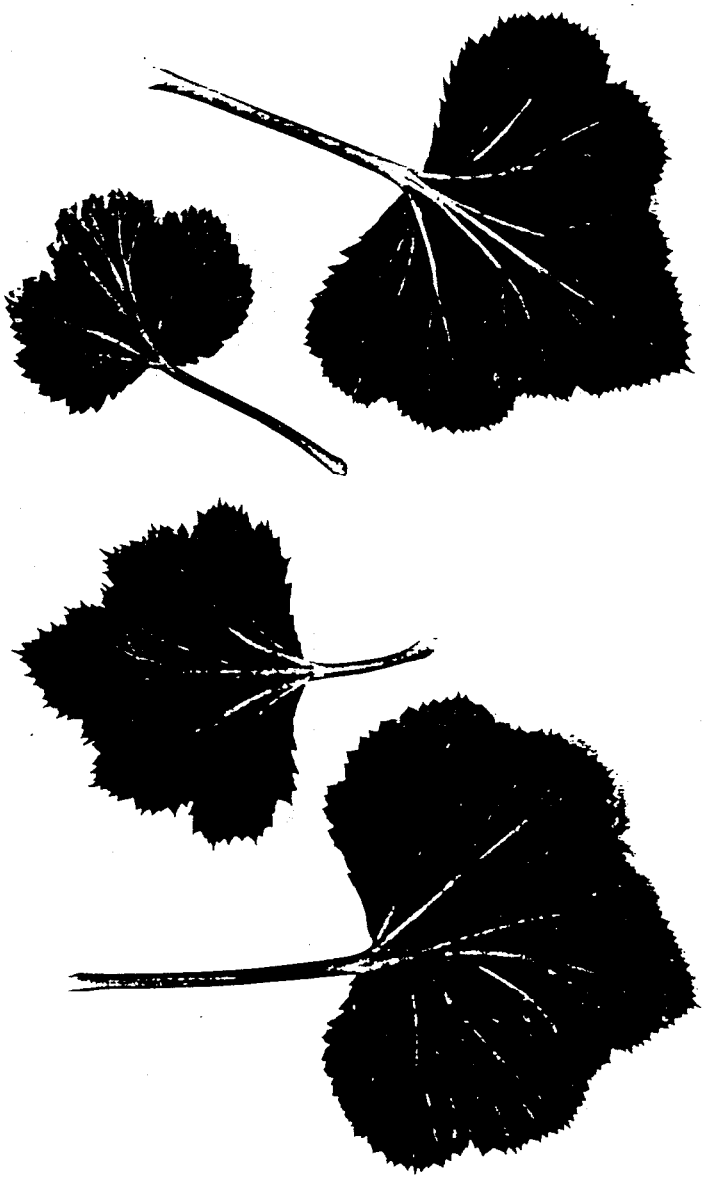

* * * * *